United States Patent
Dreyfuss

(10) Patent No.: US 8,231,653 B2
(45) Date of Patent: Jul. 31, 2012

(54) METHOD OF FORMING KNOTLESS DOUBLE ROW CONSTRUCT WITH GRAFT OR PATCH FIXED UNDER REPAIR SITE

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 268 days.

(21) Appl. No.: 12/721,958

(22) Filed: Mar. 11, 2010

(65) Prior Publication Data
US 2010/0249833 A1    Sep. 30, 2010

Related U.S. Application Data

(60) Provisional application No. 61/165,359, filed on Mar. 31, 2009.

(51) Int. Cl.
*A61B 17/04* (2006.01)
(52) U.S. Cl. ........................ 606/232; 606/301
(58) Field of Classification Search ............ 606/74, 606/103, 151, 232, 233, 301, 321, 229; 623/23.72, 623/23.75; 600/29, 30
See application file for complete search history.

(56) References Cited

U.S. PATENT DOCUMENTS

| | | | | |
|---|---|---|---|---|
| 4,233,360 A | * | 11/1980 | Luck et al. | 606/229 |
| 5,658,313 A | * | 8/1997 | Thal | 606/232 |
| 7,329,272 B2 | * | 2/2008 | Burkhart et al. | 606/232 |
| 7,803,173 B2 | * | 9/2010 | Burkhart et al. | 606/232 |
| 2007/0191849 A1 | | 8/2007 | ElAttrache et al. | |
| 2008/0027470 A1 | | 1/2008 | Hart et al. | |

* cited by examiner

*Primary Examiner* — Julian Woo
(74) *Attorney, Agent, or Firm* — Dickstein Shapiro LLP

(57) ABSTRACT

Systems and methods for soft tissue to bone repairs, without knot tying. The soft tissue repair includes the steps of (i) providing a medial row formed of a plurality of medial anchors, the medial anchors comprising suture or tape attached to each of the bodies of the medial anchors, the suture or tape forming a loop when the medial anchors are placed within tissue; (ii) passing traction sutures through each of the corresponding loop of the nearest medial anchor; (iii) passing through the tissue (rotator cuff) the free limbs of the suture or tape attached to each of the medial anchors, and one end of the traction suture (passed through the corresponding loop) at their respective points; (iv) bringing the other end of the traction suture (through a lateral cannula) underneath the tissue (the rotator cuff) and then securing the passed end of the traction suture to a graft or patch located underneath the tissue (rotator cuff); and (v) adjusting the position of the graft or patch by pulling end of the traction suture passed through the tissue (rotator cuff).

22 Claims, 3 Drawing Sheets

METHOD OF FORMING KNOTLESS DOUBLE ROW CONSTRUCT WITH GRAFT OR PATCH FIXED UNDER REPAIR SITE

CROSS-REFERENCE TO RELATED APPLICATIONS

This application claims the benefit of U.S. Provisional Application No. 61/165,359, filed Mar. 31, 2009, the entire disclosure of which is incorporated by reference herein.

FIELD OF THE INVENTION

The present invention relates to arthroscopic surgery and, more specifically, to an improved method of attaching tissue to bone, such as rotator cuff repair.

BACKGROUND OF THE INVENTION

Reattachment of soft tissue to bone employing knotless fixation devices are known in the art, particularly for the formation of double row constructs in arthroscopic rotator cuff repairs. For example, the SutureBridge™ tendon repair technique, developed by Arthrex, Inc., and disclosed in U.S. Patent Publication No. 2007/0191849, the disclosure of which is herein incorporated by reference, consists of a tied medial row constructed with two threaded suture anchors, combined with knotless lateral fixation using two Arthrex PushLocks®.

As detailed in U.S. Patent Publication No. 2007/0191849, the construct (shown above) is formed by first preparing two pilot holes for two suture anchors (with suture strands attached) that will be inserted in the medial row. Once the two suture anchors are placed in the pre-formed holes, suture tails from the suture anchors are draped over the tendon and threaded through respective eyelets of two knotless fixation devices (such as Arthrex "PushLock" C anchor, as disclosed and described in U.S. Pat. No. 7,329,272, the disclosure of which is hereby incorporated by reference in its entirety). Two pilot holes are formed (lateral from the two medial pilot holes) to accommodate the two knotless fixation devices with the suture tails threaded therethrough. A driver (with a screw inserted on a rod of the driver) is advanced to the edge of each pilot hole and used to install each knotless fixation device (and the corresponding screw) within the pilot hole to form the final construct (shown above) having an exemplary criss-cross suturing configuration. The construct enhances footprint compression and promotes tendon healing-to-bone with decreased knot tying.

The SutureBridge™ technique described above may be optionally employed in conjunction with an implant material (such as a graft or a patch of allograft or porous collagen material, that may be optionally hydrated with bone marrow aspirate), as also described in U.S. Patent Publication No. 2007/0191849. The implant material (graft or patch) is provided arthroscopically (preferably under the tissue or above the tissue) prior to implanting the lateral row of the repair system. Incorporation of the biological patch or graft underneath the tissue (for example, underneath the rotator cuff) during arthroscopic surgery necessitates the insertion of fixation devices (such as suture anchors, for example) through the patch or graft. The insertion of these fixation devices may be difficult, however, as the graft or patch is introduced and held at the surgical site in a free state which requires increased handling and instrumentation. Accordingly, a knotless double row construct with increased graft or patch fixation at the repair site is needed.

SUMMARY OF THE INVENTION

The present invention fulfills the need noted above by providing a method of forming a knotless double row construct with interpositional graft or patch fixed underneath the repair site. Medial anchors with attached suture or tape are fixated within tissue. Loops are created by the placement of the medial anchors. Traction sutures are passed through the corresponding loop of the nearest medial anchor. The free limbs of the suture or tape attached to the medial anchor, and one end of the traction suture (passed through the corresponding loop) are brought up through the tissue (rotator cuff) at their respective points. The other end of the traction sutures are brought out through a lateral cannula (underneath the tissue, i.e., the rotator cuff) and then are secured to the graft or patch. In this manner, the traction suture ends that were passed through the tissue (rotator cuff) can be used to pull the graft or patch into position. Once the graft or patch is in the desired position at the repair site, lateral anchors are employed to secure tails from the medial anchors and to complete the knotless double row fixation. The graft or patch (which may be allograft or porous collagen material, that may be optionally hydrated with bone marrow aspirate) is placed into position at the repair site without necessitating insertion of fixation devices (such as suture anchors) through the graft or patch.

These and other features and advantages of the present invention will become apparent from the following description of the invention that is provided in connection with the accompanying drawings and illustrated embodiments of the invention.

DETAILED DESCRIPTION OF THE INVENTION

Figure 1:
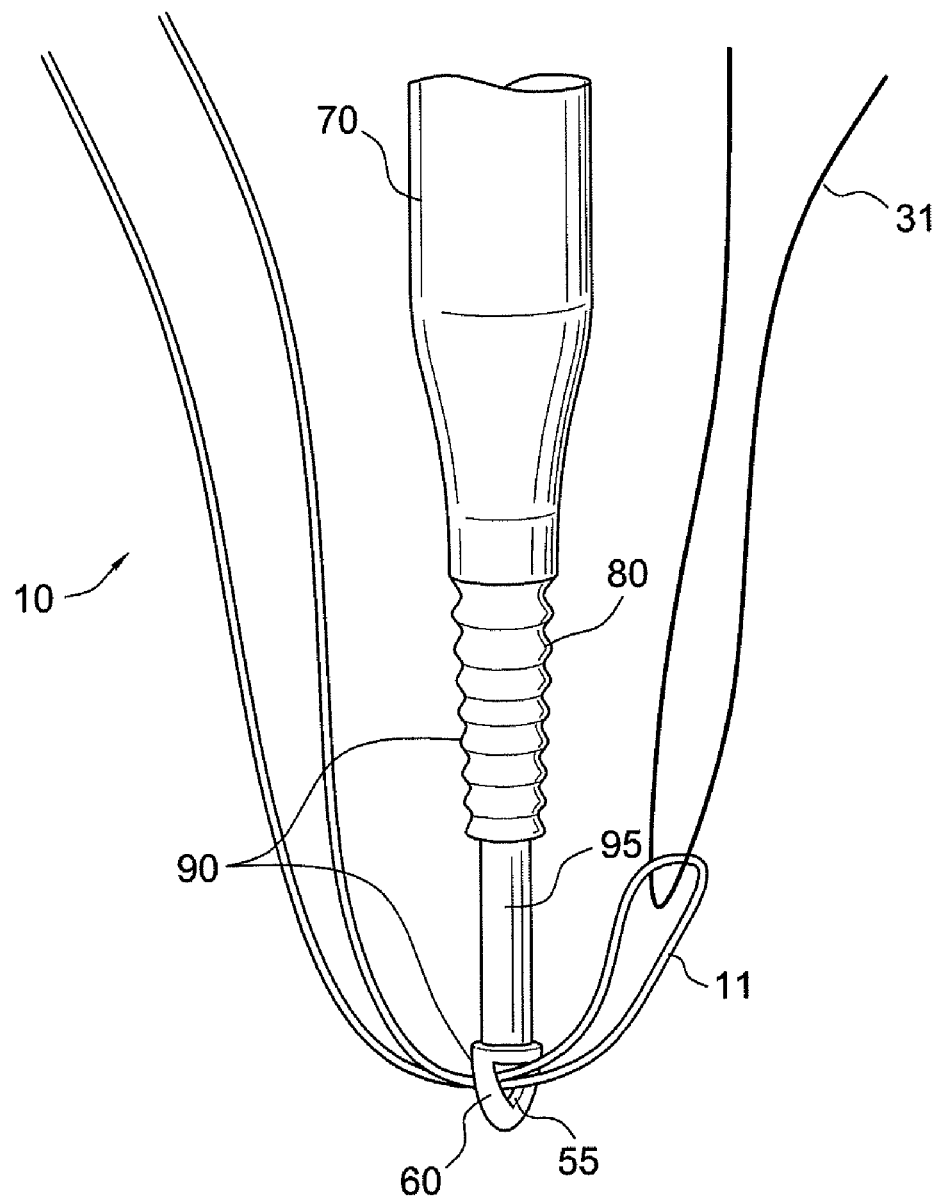
FIG. 1 illustrates a length of flexible strand (such as suture tape or suture strand) positioned on a driver and threaded through a knotless anchor (SwiveLock C anchor) to form a loop, and according to an exemplary embodiment of the present invention.

The present invention provides systems and methods of forming a knotless double row construct with interpositional graft or patch fixed underneath the repair site. Medial anchors with attached suture or tape are fixated within tissue. Loops are created by the placement of the medial anchors. Traction sutures are passed through the corresponding loop of the nearest medial anchor. The free limbs of the suture or tape attached to the medial anchor, and one end of the traction suture (passed through the corresponding loop) are brought up through the tissue (rotator cuff) at their respective points. The other end of the traction sutures are brought out through a lateral cannula (underneath the tissue, i.e., the rotator cuff) and then are tied up to the graft or patch. In this manner, the traction suture ends that were passed through the tissue (rotator cuff) can be used to pull the graft or patch into position.

Once the graft or patch is in the desired position at the repair site, lateral anchors are employed to secure tails from the medial anchors and to complete the knotless double row fixation. For example, one tail from each of the medial anchors is brought together with a tail from the adjacent medial anchor, and then the tails are secured to a corresponding lateral anchor. The remaining tails are brought together and secured to another lateral anchor.

The present invention also provides a completely knotless, double-row construct with a crossing pattern and a secured biological patch or graft underneath the tissue (for example, underneath the rotator cuff). The graft or patch (which may be allograft or porous collagen material, that may be optionally hydrated with bone marrow aspirate) is placed into position at the repair site without necessitating insertion of fixation devices (such as suture anchors) through the graft or patch.

A method of graft/patch fixation according to a method of the present invention comprises inter alia the steps of: (i) providing a medial row formed of a plurality of medial anchors, the medial anchors comprising suture or tape attached to each of the bodies of the medial anchors, the suture or tape forming a loop when the medial anchors are placed within tissue; (ii) passing traction sutures through each of the corresponding loop of the nearest medial anchor; (iii) passing through the tissue (rotator cuff) the free limbs of the suture or tape (attached to each of the medial anchors) and one end of the traction suture (passed through the corresponding loop) at their respective points; (iv) bringing the other end of the traction suture (through a lateral cannula) underneath the tissue (the rotator cuff) and then securing the passed end of the traction suture to a graft or patch located underneath the tissue (rotator cuff); and (v) adjusting the position of the graft or patch by pulling the end of the traction suture passed through the tissue (rotator cuff).

The graft or patch (which may be allograft or porous collagen material, that may be optionally hydrated with bone marrow aspirate) is placed into position at the repair site without necessitating insertion of fixation devices (such as suture anchors) through the graft or patch.

Figure 2:
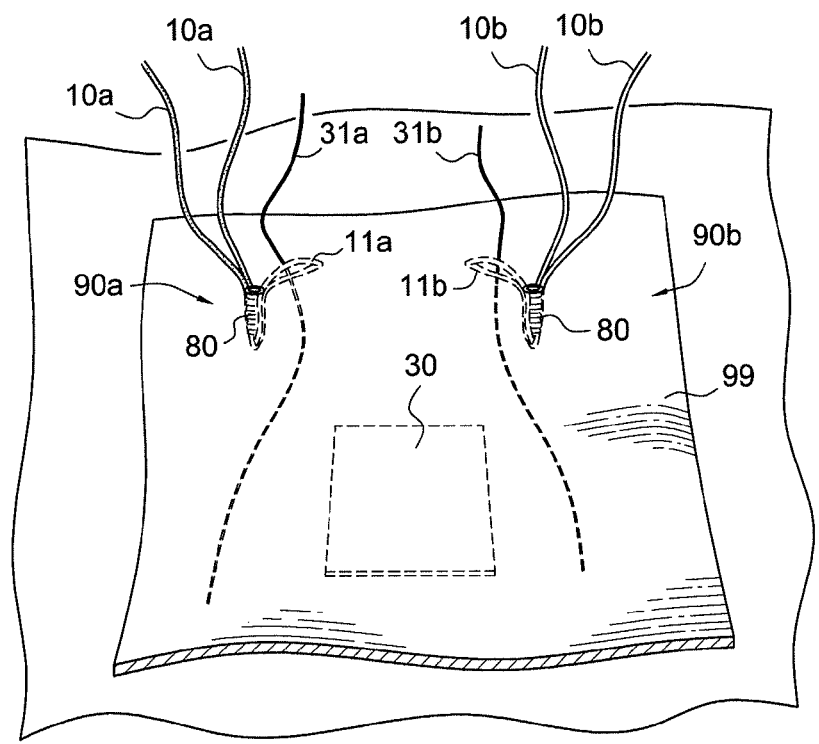
FIGS. 2-4 illustrate subsequent steps of a method of double row soft tissue repair with a graft or patch interposed at the repair site and attached to the loop of the flexible strand of FIG. 1, and according to an exemplary method of the present invention.
Figure 3:
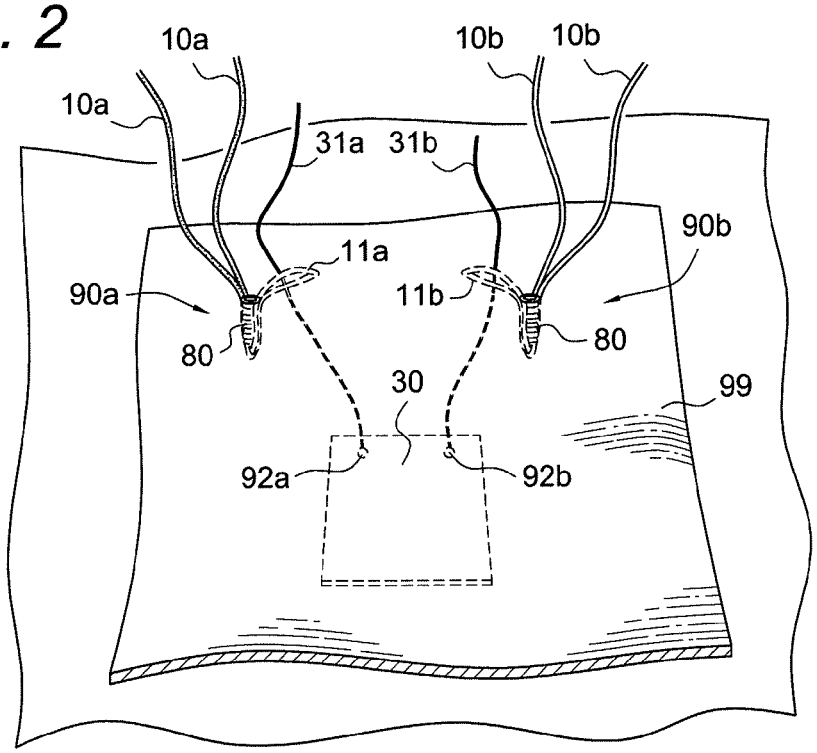
Figure 4:
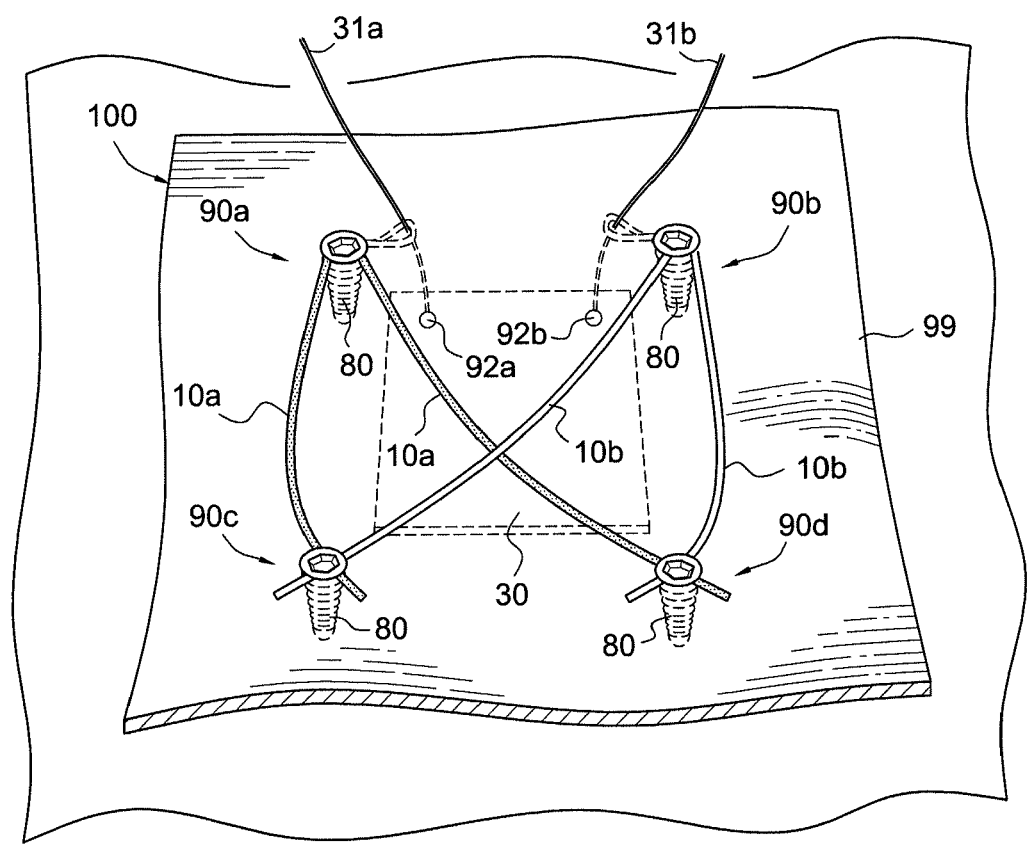

Referring now to the drawings, where like elements are designated by like reference numerals, FIG. 1 illustrates an exemplary embodiment of a length of a flexible strand 10 (suture strand or suture tape 10) passed through an eyelet of a knotless fixation device and forming a loop 11. FIGS. 2-4 illustrate exemplary steps of a method of forming a double row construct 100 with implant material (graft or patch) 30 secured to loop 11 of the suture or tape of FIG. 1.

As illustrated in FIG. 1, flexible strand (suture strand or suture tape) 10 is threaded through an eyelet 55 of a knotless fixation device 90 such as an Arthrex "SwiveLock" C anchor (as shown in FIG. 1), and as disclosed and described in U.S. Patent Application Publication No. 2007/0191849, the disclosure of which is hereby incorporated by reference in its entirety. Fixation device 90 may be also an Arthrex "Push-Lock" C anchor (as disclosed and described in U.S. Pat. No. 7,329,272, the disclosure of which is hereby incorporated by reference in its entirety).

The suture strand or tape 10 is threaded through respective eyelet 55 of tip 60 of the fixation device 90 (SwiveLock C anchor 90) to form loop 11. Driver 70 (preloaded with anchor body 80) is advanced to the edge of a pilot hole and used to install the anchor body 80 within the pilot hole. As shown in FIG. 1, loop 11 is positioned on the driver below the anchor body 80 (i.e., about 4 mm prod upon insertion). Anchor body 80 may be a screw, such as a cannulated interference screw, that is inserted over the cannulated shaft 95 of the driver and, during use, is advanced and fully seated on the driver tip. Tip 60 is configured to rotate or swivel relative to shaft 95 and anchor body 80. Tip 60 and anchor body 80 may be configured to experience a snap fit when the two pieces forming the SwiveLock C anchor 90 engage during installation (i.e., when the threaded anchor body 80 is inserted by rotational insertion to engage the anchor tip 60 and secure the suture anchor in bone).

The suture strand or tape 10 provided with loop 11 of the present invention may be employed for various soft tissue to bone repairs that employ at least one knotless fixation device in conjunction with the fixation of an implant material (such as a graft or a patch of allograft or porous collagen material, that may be optionally hydrated with bone marrow aspirate).

According to an exemplary embodiment only, the suture strand or tape 10 is employed in a method of double row fixation of tendon to bone, with increased fixation of an implant material (such as a graft or a patch of allograft or porous collagen material, that may be optionally hydrated with bone marrow aspirate) such as the one described in U.S. Patent Publication No. 2007/0191849, the disclosure of which is incorporated by reference in its entirety herewith.

FIG. 2 schematically illustrates two medial anchors 90a, 90b with respective flexible strands 10a, 10b forming respective flexible loops 11a, 11b, inserted within tissue (for example, within bone such as humerus for a rotator cuff repair) as described above with reference to FIG. 1. As noted above, the flexible strands 10a, 10b may be suture strands or suture tapes, or combinations thereof. Upon insertion within a pilot hole in the bone, two free limbs or ends of each flexible strand 10a, 10b are attached to each of the medial anchors 90a, 90b, with each of the flexible strands forming loop 11a, 11b, also attached to the respective medial anchor 90a, 90b. As detailed below, the formation of the flexible loops 11a, 11b permits another flexible strand (for example, a traction suture) to be passed through the respective loop and to aid in both the fixation of a graft or patch (by tying a knot to the graft or patch, for example) and also in the positioning of the graft or patch at the desired site.

Graft or patch 30 is provided adjacent the medial anchors 90a, 90b and, in an exemplary embodiment only, underneath the tissue (tendon such as rotator cuff) 99, as also shown in FIG. 2. Graft or patch 30 may comprise of allograft or porous collagen material, which may be optionally hydrated with bone marrow aspirate. Traction sutures 31a, 31b are employed to pull the graft or patch 30 into place and at the desired surgical location and, subsequently, as described below, to secure the graft or patch 30 at the repair site.

For each of the medial anchors 90a, 90b, the two free limbs of flexible strands 10a, 10b attached to the medial anchor, together with one end of the traction suture 31a, 31b (passed through corresponding loops 11a, 11b of the medial anchors) are then retrieved and brought up through the tissue (rotator cuff) 99 at their respective points. As shown in FIG. 2, the two free limbs of flexible strands 10a, 10b and only one end of traction suture extend above the tissue (rotator cuff).

FIG. 3 illustrates the construct of FIG. 2 but with the other end of the traction suture 31a, 31b passed (through a lateral cannula, for example) underneath the tissue (the rotator cuff) 99 and then tied up to a graft or patch 30 by knots 92a, 92b. In an exemplary embodiment, the graft or patch 30 is located underneath the tissue (rotator cuff) 99 but above the medial anchors 90a, 90b. The position of the graft or patch 30 may be adjusted at this point by simply pulling the free limb (end) of the traction suture 31a, 31b passed through the tissue (rotator cuff) 99 and extending above the tissue (rotator cuff) 99.

Reference is now made to FIG. 4. Subsequent to positioning of the graft or patch 30 into place, at the desired location, the bridge repair (final construct 100) is completed. In an exemplary embodiment only, the bridge repair may be a SutureBridge™ tendon repair technique, developed by Arthrex, Inc., and disclosed in U.S. Patent Publication No.

2007/0191849 (and as detailed above) and employing another pair of knotless fixation devices (lateral anchors) 90c, 90d. Fixation devices 90c, 90d may be similar to or different from fixation devices 90a, 90b.

To complete the formation of criss-cross pattern 100, one limb of flexible strand 10a and one limb of flexible strand 10b are brought together and retrieved from their respective medial anchor 90a, 90b, and then preloaded through an eyelet of fixation device 90c (for example, a SwiveLock C anchor 90c). Once a lateral bone socket is prepared, the two limbs of flexible strands 10a, 10b and the fixation device 90c (lateral anchor 90c) are inserted within the prepared lateral socket (employing driver 70 of FIG. 1, for example). Once the body of anchor 90c is in contact with the bone, the driver is rotated in a clockwise direction to insert the anchor body until it is flush with the bone.

Subsequently, the remaining limb of flexible strand 10a and the remaining limb of flexible strand 10b are brought together and retrieved from their respective medial anchor 90a, 90b, and then preloaded through an eyelet of another fixation device 90d (for example, a SwiveLock C anchor 90d). Once a lateral bone socket is prepared, the two limbs of the flexible strands 10a, 10b and the fixation device 90d (lateral anchor 90d) are inserted within the prepared lateral socket (employing driver 70 of FIG. 1, for example). Once the body of anchor 90d is in contact with the bone, the driver is rotated in a clockwise direction to insert the anchor body until it is flush with the bone.

In this manner, a final construct 100 (FIG. 4) is obtained, with a crossing pattern wherein medial loops 11a, 11b of the medial anchors allow increased tensioning of the flexible strands 10a, 10b and the formation of a knotless device. In an exemplary embodiment, the tissue 99 to be repaired (for example, the rotator cuff 99) is located over the graft or patch 30 but below the bridge 100 formed by crossed flexible strands 10a, 10b.

The flexible strand 10, 10a, 10b of the present invention may contain a high strength suture material with surgically-useful qualities, including knot tie down characteristics and handling, such as Arthrex FiberWire® suture disclosed in U.S. Pat. No. 6,716,234, the disclosure of which is incorporated herein by reference. The sutures may be provided with optional colored strands to assist surgeons in distinguishing between suture lengths with the trace and suture lengths without the trace.

The flexible strand 10, 10a, 10b of the present invention may be also provided in the form of a suture tape (such as the FiberTape® disclosed in U.S. Patent Publication No. 2005/0192631, the disclosure of which is herein incorporated by reference or a combination of suture strand and suture tape.

Preferably, the strands 10, 10a, 10b (including loops 11, 11a, 11b) are provided as color contrasting strands to assist surgeons in distinguishing between them while passing one limb of each strand through the loop of the other strand, as described above. For example, strands 10, 10a, 10b may be provided with tinted tracing strands, or otherwise contrast visually with the other regions of the suture (which remains a plain, solid color, or displays a different tracing pattern, for example). Accordingly, when the suture strand or tape is loaded through the eyelet of a suture anchor or passed through tissue, for example, at least one of the limbs may be visually coded, making identification and handling of the suture legs simpler.

Although the double-row construct with a crossing pattern of the present invention has been described above with reference to a biological patch or graft secured underneath the tissue (for example, underneath the rotator cuff), the graft or patch may be also placed into position at the repair site above the tissue (for example, above the rotator cuff). The method steps for the formation of a double-row construct with a crossing pattern with the graft or patch positioned above the tissue are similar in part to the method steps described above (with the graft or patch positioned underneath the tissue), but differ in that the traction sutures are passed through the tissue (i.e., through the rotator cuff) along with the suture tapes (FiberTape). As in the previously-described embodiment, the graft or patch may be allograft or porous collagen material, that may be optionally hydrated with bone marrow aspirate and/or additional blood, plasma or growth factors.

The double row construct of the present invention may be employed in surgical procedures such as rotator cuff repair, Achilles tendon repair, patellar tendon repair, ACL/PCL reconstruction, hip and shoulder reconstruction procedures, among many others.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method of fixation of soft tissue, comprising:
    securing a first plurality of fixation devices in bone, wherein at least one of the first plurality of fixation devices is a knotless fixation device with a suture loop securely attached thereto, the suture loop comprising two suture limbs extending from the suture loop;
    passing a flexible elongated member through the suture loop;
    securing one end of the flexible elongated member to an implant material to be implanted in the vicinity of a soft tissue to be repaired;
    pulling the other end of the flexible elongated material, through the soft tissue, to adjust the position of the implant material relative to the soft tissue;
    passing the two suture limbs through the soft tissue and over a lateral portion of the soft tissue; and
    anchoring the suture limbs with a second plurality of fixation devices in the bone and laterally from the first plurality of fixation devices.

2. The method of claim 1, wherein the step of securing the first plurality of fixation devices in the bone comprises passing a suture strand through an eyelet of the knotless fixation device and inserting the knotless fixation device in the bone to form the suture loop and the two suture limbs extending from the suture loop.

3. The method of claim 2, wherein the knotless fixation device is a push-in type anchor.

4. The method of claim 2, wherein the knotless fixation device is an anchor with a tip configured to rotate relative to an anchor body.

5. The method of claim 2, wherein the knotless fixation device is an anchor with a tip configured to swivel relative to an anchor body.

6. The method of claim 1, wherein the implant material is a graft or a patch.

7. The method of claim 1, wherein the implant material is selected from the group consisting of collagen, allograft and bone marrow.

8. The method of claim 1, wherein the suture loop is formed of suture or suture tape.

9. A knotless method of attaching soft tissue to bone, comprising:
provinding a first medial row constructed with a first plurality of fixation devices, wherein each of the first plurality of fixation devices is a knotless fixation device provided with a flexible strand forming a flexible loop and two free limbs securely attached to the knotless fixation device;
providing a second lateral row constructed with a second plurality of fixation devices; and
passing at least one of the two free limbs through soft tissue and over a lateral portion of the soft tissue, and securing the at least one of the two free limbs at an opposite end in a hole in bone by the second plurality of fixation devices.

10. The method of claim 9 further comprising the step of passing the flexible strand through an eyelet of a first knotless fixation device, and securing the first knotless fixation device within a bone socket so that the flexible strand forms the flexible loop and the two free limbs attached to the first knotless fixation device.

11. The method of claim 10, wherein the flexible strand is a suture or a tape.

12. The method of claim 10, wherein the first knotless fixation device is a swivel suture anchor.

13. The method of claim 10, wherein the first knotless fixation device comprises an anchor body and an anchor tip rotatably attached to the anchor body, and wherein the anchor body is configured to be inserted over the anchor tip for securing the suture anchor in bone.

14. The method of claim 13, wherein the anchor body is a cannulated interference screw.

15. The method of claim 9 further comprising the step of passing a traction suture through the flexible loop and attaching one end of the traction suture to an implant material provided adjacent to the soft tissue.

16. The method of claim 15 further comprising the step of pulling the other end of the traction suture to position the implant material at a desired location.

17. The method of claim 15, wherein the implant material is a graft or a patch.

18. A method of fixation of soft tissue, comprising:
providing a knotless fixation device having an anchor body and a tip with an eyelet, and a flexible strand passed through the eyelet;
fixing the knotless fixation device in the bone by inserting the anchor body over the tip so that the flexible strand forms a flexible loop and two limbs attached to the loop, the flexible loop and the two limbs being securely attached to the tip of the knotless fixation device;
passing a flexible elongated member through the flexible loop;
securing one end of the flexible elongated member to an implant material to be implanted in the vicinity of soft tissue to be repaired;
pulling on the other end of the flexible elongated material, through the soft tissue, to adjust the position of the implant material relative to the soft tissue; and
passing the two limbs through the soft tissue and over a lateral portion of the soft tissue, and securing the two limbs with two different fixation devices without tying a knot.

19. The method of claim 18, wherein the tip is configured to rotate relative to the anchor body.

20. The method of claim 18, wherein the tip is configured to swivel relative to the anchor body.

21. The method of claim 18, wherein the implant material is a graft or a patch.

22. A method of tissue fixation comprising:
providing a first anchor and a second anchor in the proximity of a bone, wherein each of the first and second anchors comprises a length of an elongated flexible member attached to each of the first and second anchors;
inserting the first and second anchors into first and second bone sockets so that each of the elongated flexible member forms a loop and two attached flexible legs extending from the loop, each loop being securely attached to the corresponding anchor;
passing a suture strand through each of the first and second loops;
securing one end of the suture stand to an implant material to be fixated;
pulling on the other end of the suture strand to position the implant material relative to the first and second suture anchors;
providing a plurality of bone sockets laterally displaced from the first and second bone sockets;
passing the flexible legs over a portion of a tissue to be fixated and over the fixated implant material; and
anchoring the flexible legs into the plurality of bone sockets without tying a knot and using a plurality of fixation devices, thereby providing tissue fixation.

* * * * *